(12) United States Patent
Blankenbecler et al.

US006859736B2

(10) Patent No.: US 6,859,736 B2
(45) Date of Patent: Feb. 22, 2005

(54) METHOD FOR PROTEIN STRUCTURE ALIGNMENT

(75) Inventors: Richard Blankenbecler, Stanford, CA (US); Mattias Ohlsson, Lund (SE); Carsten Peterson, Lund (SE); Markus Ringner, Lund (SE)

(73) Assignee: The Board of Trustees of the Lealand Stanford Junior University, Stanford, CA (US)

( * ) Notice: Subject to any disclaimer, the term of this patent is extended or adjusted under 35 U.S.C. 154(b) by 156 days.

(21) Appl. No.: 09/825,441

(22) Filed: Apr. 2, 2001

(65) Prior Publication Data

US 2002/0111781 A1 Aug. 15, 2002

Related U.S. Application Data

(60) Provisional application No. 60/194,203, filed on Apr. 3, 2000.

(51) Int. Cl.[7] .................. G01N 33/48; G01N 33/53; G06G 7/48
(52) U.S. Cl. ................. 702/19; 702/20; 703/11; 435/7.1; 435/501; 364/528.01
(58) Field of Search .................. 702/19, 20, 22; 703/11; 435/7.1, 501; 364/528.01, 496, 497, 578; 436/501

(56) References Cited

U.S. PATENT DOCUMENTS

| 5,642,292 A | 6/1997 | Itai et al. .................. 364/496 |
| 5,866,343 A | 2/1999 | Blom et al. .................. 435/7.1 |

OTHER PUBLICATIONS

Li. Ai–Jun. Et al. A set of van der walls and columbic radii of protein atoms for molecular and solvent–accessible surface calculation, packing evaluation, and docking . Proteins: structure, function, and genetics. 1998. vol. 32. No. 1, pp. 111–127.

Robert. C. et al. A soft, mean–field potential derived from crystal contacts for predicting protein–protein interactions. 1998, vol. 283. No. 5, pp. 1037–1047.

Knegtel. R. M. Molecular docking to ensembles of protein structures. 1997, vol. 266. No. 2, pp. 424–440.

Richard Blankenbecler; "A unified treatment of track reconstruction and particle indentification;" Computer Physics Communications 81 (1994) 225–342.

Richard Blankenbecler; "Deformable templates–revisited and extended–with an OOP implementation;" Computer Physics Communications 81 (1994) 318–334.

*Primary Examiner*—John Brusca
*Assistant Examiner*—Shubo (Joe) Zhou
(74) *Attorney, Agent, or Firm*—Lumen Intellectual Property Services, Inc.

(57) ABSTRACT

This invention provides a method for protein structure alignment. More particularly, the present invention provides a method for identification, classification and prediction of protein structures. The present invention involves two key ingredients. First, an energy or cost function formulation of the problem simultaneously in terms of binary (Potts) assignment variables and real-valued atomic coordinates. Second, a minimization of the energy or cost function by an iterative method, where in each iteration (1) a mean field method is employed for the assignment variables and (2) exact rotation and/or translation of atomic coordinates is performed, weighted with the corresponding assignment variables.

18 Claims, 4 Drawing Sheets

METHOD FOR PROTEIN STRUCTURE ALIGNMENT

CROSS-REFERENCE TO RELATED APPLICATIONS

This application is cross-referenced to and claims priority from provisional U.S. application 60/194,203 filed Apr. 3, 2000 which is incorporated herein by reference.

STATEMENT REGARDING FEDERALLY SPONSORED RESEARCH OR DEVELOPMENT

This invention was supported in part by grant number DE-AC03-76SF00515 from the U.S. Department of Energy. The U.S. Government has certain rights in the invention.

FIELD OF THE INVENTION

This invention relates generally to protein structure alignment. More particularly, the present invention relates to identification, classification and prediction of protein structures.

BACKGROUND

Proteins fold into a three-dimensional structure. The folding of a protein is determined by the sequence of amino acids and the protein's environment. Aligning proteins is a subject of utmost relevance. It enables the study of functional relationship between proteins. It also is very important for homology and threading methods in structure prediction. Furthermore, by grouping protein structures into fold families and subsequent tree reconsideration, ancestry and evolutionary issues may get unrevealed. An example of the importance of identifying protein structures can be illustrated by the comparison of DNA binding homeodomains from two organisms separated by more than 1 billion years of evolution. The yeast α2 protein and the Drosophilla engrailed protein, for example, are both regulatory proteins in the homeodomain family. Because they are identical in only 17 of their 60 amino acid residues, their relationship became certain only when their three-dimensional structures were compared.

Structure alignment amounts to matching two three-dimensional structures such that potential common substrates, e.g. α-helices, have priority. The latter is accomplished by allowing for gaps in either of the chains. Also the possibility of permuting sites within a chain may be beneficial. At first sight, the problem may appear very similar to sequence alignment, as manifested in some of the vocabulary (gap costs, etc.). However, from an algorithmic standpoint there is a major difference since the minimization problem is not trivial due to rigid body constraints. Whereas sequence alignment can be solved within polynomial time using dynamical programming methods (e.g. *Needleman S. B. & Wunsch C. D.* (1971) *Identification of homologous core structures. Proteins* 35:70–79), this is not the case for structure alignment algorithms since rigid bodies are to be matched according to these constraints. Hence, for all structure alignment algorithms the scope is limited to high quality approximate solutions.

Existing methods for structure alignment fall into two broad categories, depending upon whether one (1) directly minimizes the inter-atomic distances between the structures, or (2) minimizes the distance between substructures that are either pre-selected or supplied by an algorithm involving intra-atomic distances.

One approach is an iterative dynamical programming method (e.g. Laurants D.V. et al. (1993) *Structural similarity of DNA-binding domains of bacteriophage repressors and the globin core. J. Mol. Biol.* 3:141–148; and *Gerstein M. & Levitt M.* (1996) *Using iterative dynamic programming to obtain accurate pairwise and multiple alignments of protein structures. In: Proceedings of the 4$^{th}$ International Conference on Intelligent Systems in Molecular Biology*, Menlo Park, Calif.: AAAI Press). In this approach one first computes a distance matrix between all pairs of atoms (e.g. Cα) forming a similarity matrix, which by dynamical programming methods gives rise to an assignment matrix mimicking the sequence alignment procedure. One of the chains is then moved towards the other by minimizing the distance between assigned pairs. This method does not allow for permutations, since the internal ordering is fixed by construction. In another inter-atomic approach the area rather than the distances between two structures is minimized (e.g. U.S. Pat. No. 5,878,373). In yet another approach, one compares distance matrices within each other of the two structures to be aligned, which provide information about similar structures (e.g. *Holm L. & Sander C.* (1993) *Protein structure comparison by alignment of distance matrices. J. Mol. Biol.* 233:123–138; and *Lu G.* (2000) *A new method for protein structure and similarity searches. J. Appl. Cryst.* 33:176–183). The similar structures are subsequently matched. In these methods, for instance by Holm & Sander as well as by Lu, permutations can in principle be dealt with.

However, there are implementation issues shared by both types of methodologies mentioned above. One is structure encoding (Cα and/or Cβ of the chains). For many methodologies Cα appears to be sufficient, whereas in some cases Cβ is needed. Also, the choice of distance metric is a subject of concern in order to avoid the influence of outliers.

The present methods are useful in certain types of problems of protein structure alignment and less useful in others. Some methods only partially explore the space of possible alignments or lack the ability to handle permutations efficiently. In addition, as mentioned above, the minimization problem for protein structure alignment is non-trivial due to the rigid body constraint. Accordingly there is a need to develop a general method that not only provides an acceptable solution for the minimization problem, but also has a high assurance of protein structure alignment and prediction and thereby applicable to a variety of problems.

SUMMARY OF THE INVENTION

This invention relates generally to protein structure alignment. More particularly, the present invention relates to identification, classification and prediction of protein structures. The present invention involves two key ingredients. First, an energy or cost function formulation of the problem simultaneously in terms of binary (Potts) assignment variables and real-valued atomic coordinates. Second, a minimization of the energy or cost function by an iterative method, where in each iteration (1) a mean field method is employed for the assignment variables and (2) exact rotation and/or translation of atomic coordinates is performed, weighted with the corresponding assignment variables.

In accordance with exemplary embodiments of the present invention, a method is provided with a plurality of steps with the purpose of aligning two three-dimensional protein structures. In that respect the method receives a first protein with N1 atoms and a second protein with N2 atoms. An initial alignment of the atoms of the first protein to the atoms of the second protein is made. Once the initial alignment is made, all atomic distances between the coordinates of the atoms of the first protein and the atomic coordinates of the atoms of the second protein can be calculated. These distances could be represented in any type of distance matrix using the real-valued atomic coordinates. Subsequently, the present invention provides for a mechanism to define a matrix with a plurality of binary assignment variables wherein each binary assignment variable corresponds to either a match or to a gap (i.e. not a match). Upon defining the binary assignment variables, the present invention defines one or more mean field equations wherein the plurality of binary assignment variables are now replaced by a plurality of continuous mean field variables, whereby each mean field variable has assigned a value between 0 and 1. The mean field equations also include a plurality of forces that are proportional to the atomic distances squared. The present invention provides for the formulism of an energy function wherein four different costs are included. First, the energy function includes a cost for each atomic distance wherein the distance is based on a weighted body transformation using the continuous mean field variables of the first protein while keeping the second protein fixed. Second, the energy function includes a cost $\lambda$ for each gap that is created by either the first protein or the second protein. Third, the energy function includes a cost 67 for a position-independent consecutive gap that is created. Finally, fourth, the energy function includes a cost for enforcing a constraint to satisfy that each atom of the first protein either aligns with the atom of the second protein or to a gap. In addition, an optional fifth cost could be included in the energy function to discourage any crossed matches. The energy function is minimized by an iterative process wherein the continuous mean field variables are updated using the mean field equations for a decreasing set of temperatures T until convergence to a predefined convergence value is reached. Once the iterative process has been completed, i.e. after convergence, the continuous mean field variables are rounded of to either 0 or 1.

In view of that which is stated above, it is the objective of the present invention to provide for an extensive search of all possible alignments, including those involving arbitrary permutations. It is another objective of the present invention to allow for arbitrary weighting of a selected atom site assignment. It is yet another objective of the present invention to demand a match between selected amino acids in desirable geometric arrangements for certain biological functionality. It is still another objective of the present invention to provide for methods so that by adjusting the gap cost parameters for each site, the method can find matches of selected segments of the protein chains. It is still another objective of the present invention to provide for the inclusion of user prescribed constraints. It is another objective of the present invention to allow for a probabilistic interpretation of the results. The advantage of the present invention over the prior art is that it provides a generic and flexible method which is able to handle protein permutations efficiently.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
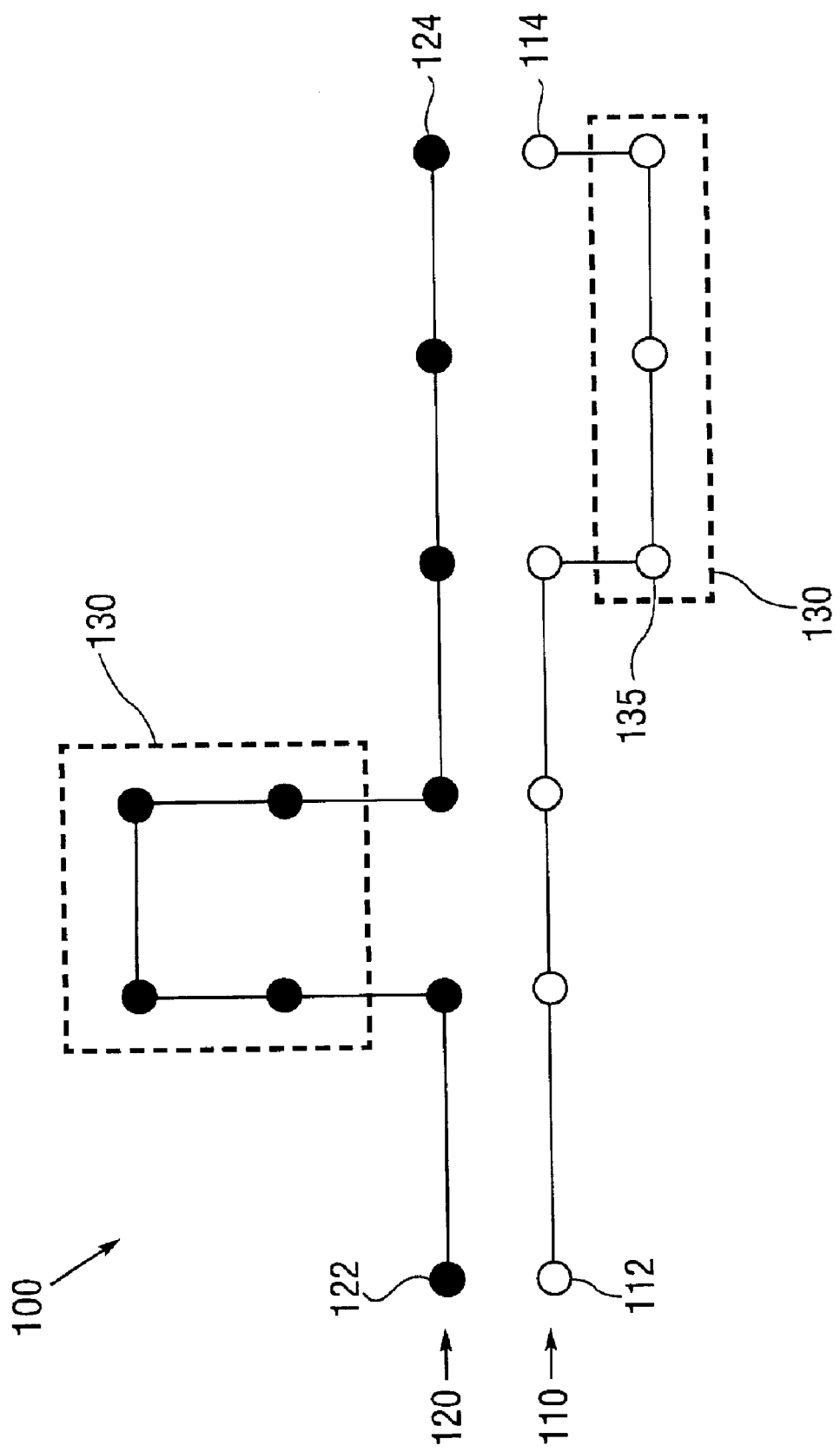
FIG. 1 illustrates an example of two exemplary chains.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Algorithm 1

The present invention can be understood according to the following exemplary embodiments in which there are two proteins, protein 1 and protein 2 with respectively $N_1$ and $N_2$ atoms, that are to be structurally aligned. In the general sense of the present invention, the structural alignment is accomplished by a series of weighted rigid body transformations of the first chain, keeping the second chain fixed. The atom coordinates of the first and the second chain of protein 1 and 2, respectively, is denoted by $x_i$ (i=1, ... , $N_1$) and $y_j$ (j=1, ... , $N_2$). The word "atom" will be used throughout this description in a generic sense—it could represent individual atoms but also groups of atoms. In the present exemplary embodiment, it could mean C$\alpha$ atoms along the backbone. It could also mean e.g. center-of-mass of side-chain atoms. A square distance metric between the chain atoms is used according to EQ. 1, for instance $$d_{ij}^2 = |x_i - y_j|^2 \quad (1)$$

but the formalism is not confined to this choice. In general, any distance metric could be used as long as it provides a measure for all distances between the atom coordinates of the first and second chain of protein 1 and 2. In the description of the present invention that follows, first the encoding method and energy (or cost) function is discussed using Algorithm 1, including a discussion of the method for minimizing this energy function. In addition, the description will distinguish a gapless case wherein all atoms of the first and second chain are matched with each other versus a gapped case wherein it is allowed to have a gap in either of the chains meaning that an atom in for instance the first chain is not connected to the second chain. Finally, an alternative way for calculating the energy function is provided in Algorithm 2 which is more efficient for alignments where no permutations are expected.

Gapless Case

To better illustrate the present invention, the discussion will start off with the gapless case with $N_1=N_2$. First binary assignment variables $s_{ij}$ are defined, such that $s_{ij}=1$ if atom i in one chain matches j in the other chain and $s_{ij}=0$ otherwise. Since every atom in one chain must match one atom in the other, the following conditions must be fulfilled:

$$\sum_{i=1}^{N_1} s_{ij} = 1 \quad j = 1, \ldots, N_2 \quad (2)$$

$$\sum_{j=1}^{N_2} s_{ij} = 1 \quad i = 1, \ldots, N_1 \quad (3)$$

A suitable energy function to minimize subject to the above constraints (EQS. 2 and 3) is $$E_{chain} = \sum_{i=1}^{N_1} \sum_{j=1}^{N_2} s_{ij} d_{ij}^2 \qquad (4)$$

where the spatial degrees of freedom, $x_i$, are contained in the distance matrix $d^2_{ij}$. Thus whenever $s_{ij}=1$ one adds a penalty $d^2_{ij}$ to $E_{chain}$. Note that EQ. 4 is to be minimized both with respect to the binary variables $s_{ij}$ and the real-valued coordinates $x_i$.

Gapped Case

Allowing for gaps in either of the chains is implemented by extending $s_{ij}$ to include 0-components in a compact way; $s_{i0}=1$ and $s_{0j}=1$ if an atom (i~or~j) in one chain is matched with a gap in the other and vice versa. Hence, gap positions are not represented by individual elements in $s_{ij}$; rather the gap-elements correspond to common sinks. The matrix S, with elements $s_{ij}$, containing gap-elements is shown in EQ. 5.

$$\begin{pmatrix} & & & & s_{0N_2} \\ & s_{01} & s_{02} & & \\ s_{10} & s_{11} & s_{12} & \cdots & s_{1N_2} \\ & & & \cdots & \\ s_{20} & s_{21} & s_{22} & \cdots & s_{2N_2} \\ \vdots & & & & \\ s_{N_10} & s_{N_11} & s_{N_12} & \cdots & s_{N_1N_2} \end{pmatrix} \qquad (5)$$

Some caution is needed when generalizing EQS. 2 and 3 to host gaps, since the elements of the first row and column (gap-mappings containing the index 0) in EQ. 5 differ from the others in that they need not sum up to 1. Hence EQS. 2 and 3 become $$\sum_{i=0}^{N_1} s_{ij} = 1 \quad j = 1, \ldots, N_2 \qquad (6)$$

$$\sum_{j=0}^{N_2} s_{ij} = 1 \quad i = 1, \ldots, N_1$$

where the first condition can be written as $$\sum_{i=1}^{N_1} s_{ij} = 1 \text{ or } \sum_{i=1}^{N_1} s_{ij} = 0; \quad j = 1, \ldots, N_2 \qquad (7)$$

Figure 2:
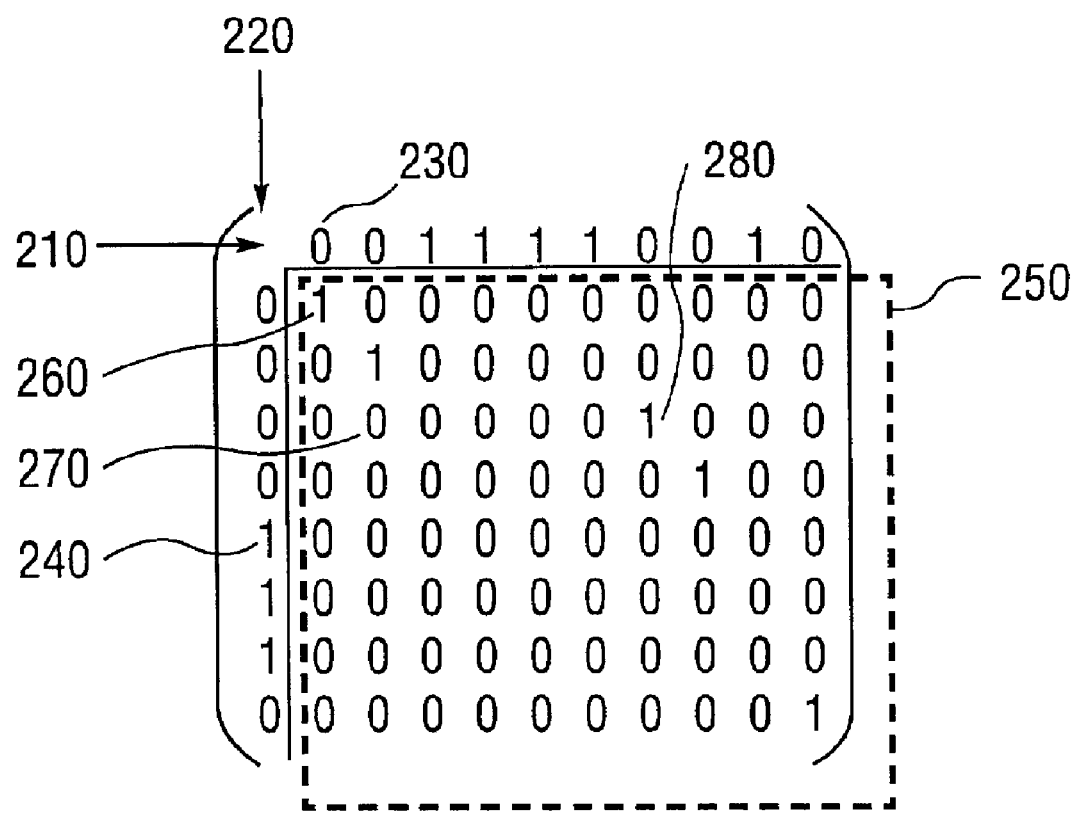
FIG. 2 illustrates an example of the assignment matrix S corresponding to the matching of two exemplary chains.

An illustrative example of the encoding ($s_{ij}$) of matches and gaps is shown in FIGS. 1 and 2. In FIG. 1, 100 shows two chains, I and J, by respectively 110 and 120. The first atom in chain I is indicated by 112 as i=1. The first atom in chain J is indicated by 122 as j=1. Analogously, the last atom in chain I is indicated by 114 as i=8, whereas the last atom in chain J is indicated by 124 as j=10. In FIG. 1, an example of a gapless situation is for instance when atom 112 and 122 are matched in the first position for both atom i and j. In FIG. 1, an example of a gapped situation is for instance when atom i or j do not match each other as is indicated by 130. In FIG. 2, FIG. 1 is now represented as a matrix S as shown by 200. In FIG. 2, 210 is the 0-row for chain 110, i.e. chain I, indicating whether an atom in chain 110 is matched with an atom of chain 120 or matched with a gap; i.e. indicated by respectively 0 (match) or a 1 (gap). Similarly, in FIG. 2, 220 is the 0-column for chain 120, i.e. chain J, indicating whether an atom in chain 120 is matched with an atom of chain 110 or matched with a gap; i.e. indicated by respectively 0 (match) or a 1 (gap).

For instance, $s_{01}$ as indicated by 230 is 0 which means that the particular atom (i.e. j=1) in chain J has a match, whereas $s_{50}$ as indicated by 240 is 1 which means that the particular atom (i.e. i=5) in chain I is matched with a gap. This latter example is also shown in FIG. 1 by 135 where atom in chain I is not matched with chain J, but matched with a gap.

In FIG. 2, the binary numbers in the matrix indicated by 250 correspond to which particular atom of I and J match with each other. Here a 0 means that there is no match, and a 1 means a match between the particular atoms in both chains. For instance, 260 shows $s_{11}$ as 1 indicating that atom in position i=0 matches atom in position j=1. Another example is given by 270 which shows $s_{32}$ as 0 indicating that atom in position i=3 does not match atom in position j=2. On the contrary as shown by 280, atom in position i=3 matches atom in position j=7 as indicated by a 1.

Assuming a constant penalty per inserted gap one has the error function $$E = E_{chain} + \sum_{i=1}^{N_1} \lambda_i^{(1)} s_{i0} + \sum_{j=1}^{N_2} \lambda_j^{(2)} s_{0j} \qquad (8)$$

where $\lambda_i^{(1)}$ is the cost for matching atom i in the first chain with a gap in the second chain, and similarly for $\lambda_j^{(2)}$. The position dependence of the gap costs, $\lambda_i^{(1)}$ and $\lambda_j^{(2)}$, originates from the fact that it is desirable not to break $\alpha$-helix and $\beta$-strand structures.

In EQ. 8 the gap penalties are proportional to gap lengths. In sequence alignment it is conjectured that gap penalties consist of two parts; (1) a penalty for opening a gap and then (2) a penalty proportional to the gap length. The present invention includes a similar gap cost philosophy as presented by Gerstein & Levitt (Gerstein M. & Levitt M. (1996) Using iterative dynamic programming to obtain accurate pairwise and multiple alignments of protein structures. In: *Proceedings of the 4th International Conference on Intelligent Systems in Molecular Biology*, Menlo Park, Calif.: AAAI Press), i.e. $\lambda_i^{(1)}$ and $\lambda_j^{(2)}$ for opening a gap and a position-independent $\lambda$ per consecutive gap. Hence, EQ. 8 generalizes to $$E = E_{chain} + \sum_{i=1}^{N_1} \lambda_i^{(1)} s_{i0} + \sum_{j=1}^{N_2} \lambda_j^{(2)} s_{0j} + \qquad (9)$$

$$\sum_{i=1}^{N_1} (\delta - \lambda_i^{(1)}) s_{i-1,0} s_{i0} + \sum_{j=2}^{N_2} (\delta - \lambda_j^{(2)}) s_{0j-1,0} s_{0j}$$

where products like $s_{i-1,0} s_{i0}$ are 1 if two adjacent atoms are matched to gaps.

In addition, it may also be desirable to discourage "crossed" matches. Cross matches are matches in which i is matched to j, and (i+1) is matched to k, where k<j, or matches in which (i−1) is matched to k, where k>i. This could be accomplished by adding the term according to $$E_{crossed} = \omega \sum_{i,j} s_{i,j} \left\{ \sum_{k<j} s_{(i+1),k} + \sum_{k>j} s_{(i-1),k} \right\} \qquad (10)$$

where $\omega$ is defined as the strength of this penalty term.

Minimization

The next aspect that is needed is an efficient procedure for minimizing E with respect to both $s_{ij}$ and $x_i$ subject to the constraints in EQS. 6 and 7. As mentioned above, this minimization problem is non-trivial due to the rigid body constraint. Earlier in 1992, Ohlson et al. probed that a mean field approximation could be used for fitting structures with relevance factors in case of track finding problems with a template approach (*Ohlson M., Peterson C. & Yuille A. L.* (1992) *Track finding with deformable templates—the elastic arms approach. Comp. Phys. Comm.* 71:77–98).

In the present invention, a mean field approximation approach is integrated, however this mean field method is different from any previously mentioned mean field approaches (see e.g. *Blankenbecler R.* (1994) *Deformable templates—revisited and extended—with an OOP implementation. Comp. Phys. Comm.* 81:318–344, 1994). In the paper by Blankenbecler (1994), the assignment matrix, S(ij), although as they are also denoted by v(ij) and V(ij), assigns a "hit" (spark) in a particle detector to track a mathematical curve representing the path of the high energy particle. In the present invention, the mean field approach is employed for a protein matching case in which it assigns for instance a carbon alpha (atom) in one chain to a carbon alpha (atom) in another chain. During the iteration/calculation, while the v's are not exactly zero or one, they can be interpreted as the "probability" that atom i in one chain is assigned to atom j in the other chain. For an introduction on the mean field approach one could refer to the paper by *Peterson C. & Soderberg B.* (1989) *A new method for mapping optimization problems onto neural networks, Int. J. Neural. Syst.* 1:3–22.

In the formulation of the present invention, the inherent optimization difficulty resides in the binary part ($s_{ij}$) of the problem. Hence, minimizing EQ. 9 using a simple updating rule for $s_{ij}$ will very likely yield poor solutions due to local minima. Well known stochastic procedures such as simulated annealing (e.g. *Kirkpatrick S., Gelatt C. D. & Vecchi M. P.* (1983) *Optimization by simulated annealing. Science* 220:671–680) for avoiding these local minima are too costly from a computational standpoint. In the mean field approach of the present invention, the philosophy behind simulated annealing is retained, but the tedious simulations are replaced by an efficient deterministic process. The binary variables $s_{ij}$ are then replaced by continuous mean field variables $v_{ij}$, whereby $v_{ij}$ is a value between 0 and 1, with a dynamics given by iteratively solving the mean field equations for a decreasing set of temperatures T down to $T_0$, where most of the $v_{ij}$ approach either 1 or 0. These continuous mean field variables can evolve in a space not accessible to the original intermediate variables. The intermediate configurations at non-zero T have a natural probabilistic interpretation.

For $s_{ij}$ satisfying EQ. 6, the mean field equations for the corresponding $v_{ij}$ read $$v_{ij} = \frac{e^{u_{ik}/T}}{\sum_{k=0}^{N_2} e^{u_{ik}/T}}; \quad i=1, \ldots, N_1 \quad (11)$$

where the force $u_{ij}$ is given by $$v_{ij} = -\frac{\partial E}{\partial v_{ij}} \quad (12)$$

and is computed by substituting $s_{ij}$ with $v_{ij}$ in E (EQ. 9). Note that the desired normalization condition, EQ. 6

$$\sum_{j=0}^{N_2} v_{ij} = 1; \quad i=1, \ldots, N_1 \quad (13)$$

is fulfilled automatically in EQ. 11. The other condition (EQ. 7) is enforced by adding a penalty term $$E_\gamma = \gamma \sum_{j=1}^{N_2} \left[ \left( \sum_{i=1}^{N_1} v_{ij} \right) \left( \sum_{k=1}^{N_1} v_{kj} - 1 \right) \right] \quad (14)$$

$$= \gamma \sum_{i=1}^{N_1} \sum_{k \neq i}^{N_1} \sum_{k=1}^{N_2} v_{ij} v_{kj}$$

where $\gamma$ is a parameter and the last equality follows from the fact that $v^2_{ij} = v_{ij}$ for T=0.

So far the description only described the assignment part when minimizing the error function. When updating the mean field variables $v_{ij}$, using the mean field equations, the distance measure $d^2_{ij}$ is a fixed quantity. This corresponds to having the chains at fixed positions. However, the present invention also includes the step to minimize the distance between the two chains. Based on the probabilistic nature of the mean field variables, the chain positions are updated using the (probabilistic) assignment matrix V, with elements $v_{ij}$. This is done simultaneously with the updating of $v_{ij}$. Explicitly, one of the chains will be moved in order to minimize the chain error function $E_{chain}$ (EQ. 4).

The distance measure $d^2_{ij}$ depends on the translation vector a and the rotation matrix R making a total of six independent variables. Let $x'_i$ be the coordinates of the translated and rotated protein, i.e. $x'_i = a + R x_i$, then $$E_{chain} = \sum_{i=1}^{N_1} \sum_{j=1}^{N_2} v_{ij} (a + R x_i - y_j)^2 \quad (15)$$

This minimization problem can be solved exactly with closed-form expressions for R and a that minimizes $E_{chain}$ as was pointed out by Neuman (1937) in a paper entitled "*Some matrix-inequalities and metrization of matric-space*" in *Tomsk. Univ. Rev. vol.* 1, *pp.* 286–300. It should be noted that this solution is rotationally invariant (independent of R) for the special case when the atoms in the two chains matches each other with the same weight, i.e. when vij=constant for all i and j, which is the case for high T.

In summary, for a decreasing set of temperatures T, one iterates until convergence:

1. The mean field equations (EQ. 11), and
2. Exact translation and rotation of the chain (EQ. 15)

It is stressed that in the present invention, step 2, i.e. the translation and rotation of the chain, is done with the probabilistic mean field assignment variables $v_{ij}$ and not with the binary variables, $s_{ij}$. After convergence, $v_{ij}$ are rounded off to 0 or 1 and rms (root-mean-square-distance) is computed for the matching pairs. An exemplary detail of the algorithmic details can be found in the next subsection.

The forces $u_{ij}$ entering EQ. 11 are proportional to $d^2_{ij}$ (EQS. 4 and 12). It is the ratio $d^2_{ij}/T$ that counts. Hence, for large temperatures T, $v_{ij}$ is fairly insensitive to $d_{ij}$ and many potential matching pairs (i,j) contribute fairly evenly. As the temperature is decreased, a few pairs (the ones with small $d_{ij}$ are singled out and finally at the lowest T only one winner remains. One can view the situation as that around each atom i one has a Gaussian domain of attraction, which initially (large T) has a large width, but gradually shrinks to a small finite value.

Figure 3:
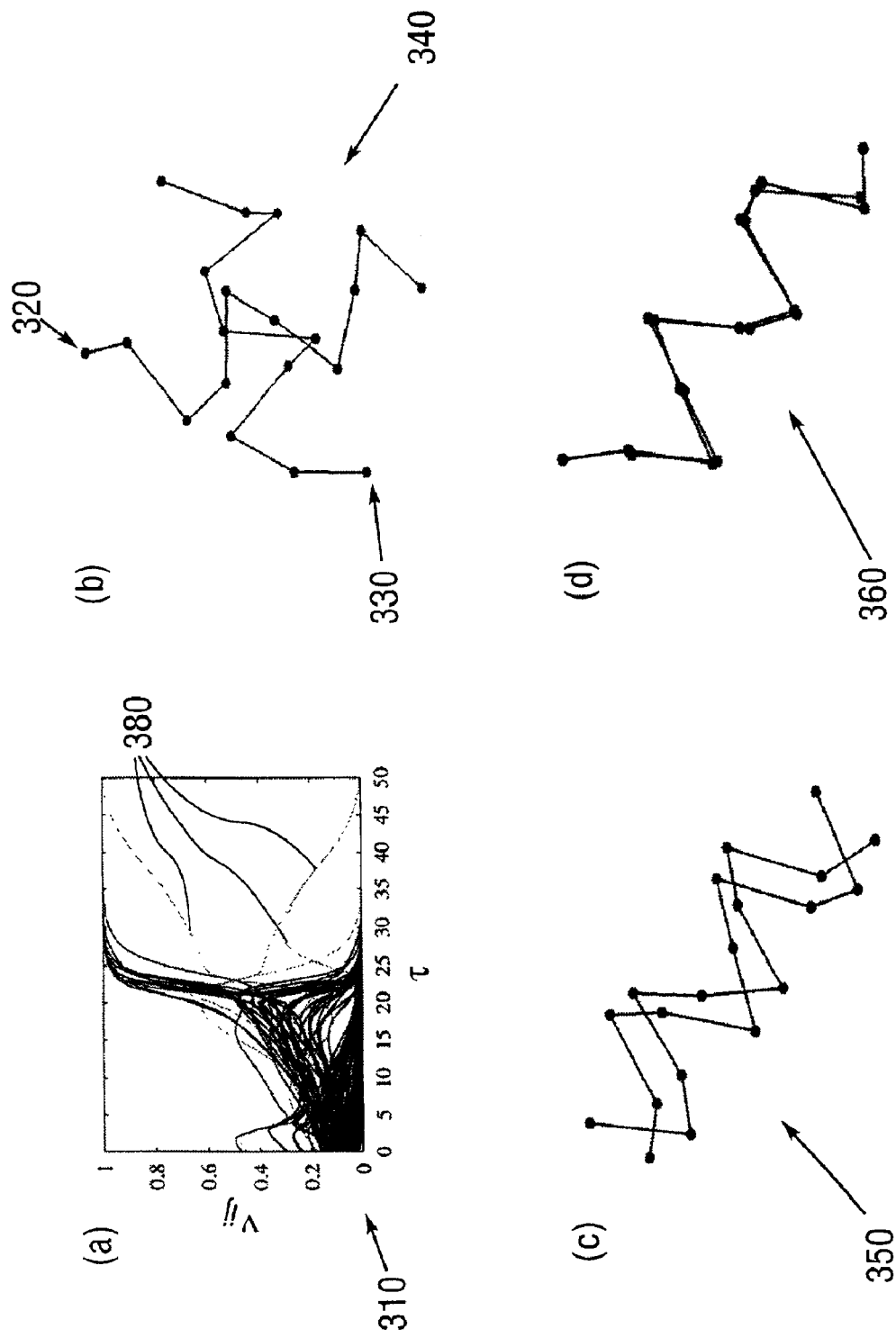
FIG. 3 illustrates the probabilistic nature of the approach and an exemplary alignment process.

The probabilistic of the approach is shown in FIG. 3 by 310, where the evolution of $\upsilon_{ij}$, as T is lowered, is shown for parts of the first helices of exemplary proteins 1 and 2 that are used for illustrative purposes together with snap-shots of the corresponding chain sections. Protein 1 and 2 are shown in FIG. 3 by respectively 320 and 330. Evolution of all the 120 $\upsilon_{ij}$ as a function of iteration time $\tau$ (T is lowered with $\tau$). At high T all $\upsilon_{ij}$ are similar; all potential matches have equal probability. At lower T, several $\upsilon_{ij}$ have approached 0 or 1 and the movable chain is moving in the right direction. At yet lower T, note that a few $\upsilon_{ij}$ converge later than the majority. These are in this example related to the matching of the last atom in one of the chains. This atom has two potential candidates to match resulting in a number of $\upsilon_{ij}$ that converge last.

An illustrative example of the alignment is shown in FIG. 3 by 340, 350 and 360 for 10 atoms in the first helices in the protein 1 indicated by 320 and protein 2 indicated by 330. In FIG. 3, 340 shows the positions of the atoms at $\tau=1$. For high T every atom in a protein feels all the atoms in the other protein and the problem is rotationally invariant. As shown in FIG. 3 by 350, for $\tau=12$ most of the relevant matchings are forcing the system to move in the right direction. As shown in FIG. 3 by 360, for $\tau=50$ the final assignments are complete according to a predefined convergence value. The different snapshots in FIG. 3 are presented using different projections. Some $\upsilon_{ij}$ approach 0 or 1 rather late and are indicated in FIG. 3 by 380. These $\upsilon_{ij}$ are related to the atom at the end of the protein 1. The difficulty is whether to align this atom to the last or second last atom in protein 2.

Algorithm 2

In this section an alternative formulation of the energy function will be described. This alternative algorithm, called Algorithm 2, is more efficient for alignments where no permutations are expected than Algorithm 1. Algorithm 2 can be described as a shortest path algorithm with a varying distance matrix. In that case, the energy function that is to be minimized is now $$E=\Sigma_{i,j} D_{i,j} \tag{16}$$

The $D_{i,j}$ elements are referred to as the optimal alignment energy cost elements from point (ij) to the "end" of the protein chain. These elements are computed by the following scheme $$D_{i,j}=V_{i,j}^{1}(D_{i,(j+1)}+\lambda_j^2+V_{i,(j+1)}^1(\delta-\lambda_j^2))+V_{i,j}^2(D_{(i+1),(j+1)}+d_{i,j}^2)+V_{i,j}^3(D_{(i+1),j}+\lambda_j^1+V_{(i+1),j}^3(\delta-\lambda_j^1)) \tag{17}$$

In these EQS. 16 and 17, the various quantities are basically extensions of the parameters introduced and discussed in Algorithm 1 above. The various quantities as in EQ. 17 are defined as

| | |
|---|---|
| $d_{i,j}^2$ | square distance between chain atoms |
| $\lambda_i^1$ | energy for matching atom i in protein 1 to a gap |
| $\lambda_j^2$ | energy for matching atom j in protein 2 to a gap |
| $\delta$ | energy for position-independent con sec utive gap |
| $V_{i,j}^1$ | = "right neuron" = 1 if j matches a gap |
| $V_{i,j}^2$ | = "match neuron" = 1 if j matches i |
| $V_{i,j}^3$ | = "down neuron" = 1 if i matches a gap |
| $P_{i,j}$ | = probability of ending up at position (i,j) (see EQ. 20) |

Using the alternative formulation, the mean field variables are now updated by updating equations $$u_{i,j}^1=(D_{i,(j+1)}+\lambda_j^2+V_{i,(j+1)}^1(\delta-\lambda_j^2))$$

$$u_{i,j}^2=(D_{(i+1),(j+1)}+d_{i,j}^2)$$

$$u_{i,j}^3=(D_{(i+1),j}+\lambda_j^1+V_{(i+1),j}^3(\delta-\lambda_j^1)) \tag{18}$$

As will also become clear in the subsequent section where both algorithm 1 and 2 are listed and compared, the Potts mean variables are now updated similar as in Algorithm 1, namely $$V_{i,j}^k = \frac{\exp(-u_{i,j}^k/T)}{\sum_l -u_{i,j}^l/T} \tag{19}$$

and finally, the matching or assignment matrix is given by $$\text{Matching Matrix}=S_{i,j}=P_{i,j}V_{i,j}^2 \tag{20}$$

In other words, this means that the probability for matching (ij) is equal to the product of the probability of ending up at position (ij) and the probability of matching that particular pair.

Implementation

The method presented in the present invention can be applied to, but is not limited to, different types of proteins each with its own type of difficulty in terms of structure alignment. For instance, Dihydrofolate Reductases which contain ($\alpha$- and $\beta$-proteins that have mainly parallel beta sheets, Globins that are all-$\alpha$, Plastocyanin/azurin and Immunoglobulins which are both are proteins that all-$\beta$, and Permutated (winged helix fold) proteins. The latter example is a protein group that is considered difficult and where iterative dynamical programming will fail. In the next sections examples are provided for implementation of the algorithm and the parameters involved. This section contains three parts, i.e. parameters, initialization, and iteration steps.

Parameters

In general, two kind of parameters are used; the ones related to the encoding of the problem ($\gamma$) and iteration dynamics ($\epsilon$), where $\epsilon$ governs the annealing schedule as shown in the Table 1 below, and the ones specifying gap costs ($\lambda$, $\delta$). The same set of parameters can be used for most of the pairs as shown in the Table 1 below. The first protein family shown in Table 1 involves 27 pairs, whereas the others one each. The algorithm is remarkably stable. The value of $\lambda$ for each carbon alpha site is chosen to reflect the importance of the surrounding substrate structure, such as an ($\alpha$-helix, $\beta$-sheet, and others. Sheet and helix refer to secondary structure assignment for each C$\alpha$ atom.

TABLE 1

| Protein Family | $\epsilon$ | $\gamma$ | $\lambda$ | $\lambda$ sheet | $\lambda$ helix | $\delta$ |
|---|---|---|---|---|---|---|
| $\alpha$, $\beta$, all-$\alpha$ | 0.8 | 0.065 | 0.10 | 1.5 $\lambda$ | 1.5 $\lambda$ | $\lambda$/2 |
| Plastocyanin/azurin | 0.8 | 0.035 | 0.10 | 2.0 $\lambda$ | 2.0 $\lambda$ | $\lambda$/5 |
| Immunoglobulins | 0.8 | 0.040 | 0.15 | 2.0 $\lambda$ | 2.0 $\lambda$ | $\lambda$/5 |
| Winged helix fold | 0.8 | 0.070 | 0.20 | 2.0 $\lambda$ | 2.0 $\lambda$ | $\lambda$/5 |

Initialization

An initialization of the chains is made prior to the mean field alignment. First both chains are moved to their common center of mass. For a random initialization, this move is then followed by a random rotation of one of the chains. Most of the times, however, a sequential initialization is used that consists of minimizing EQ. 4 using a band-diagonal assignment matrix S. This corresponds to a situation where, on the average, atom i in one of the chains is matched to atom i in the other.

Iteration Steps

Figure 4:
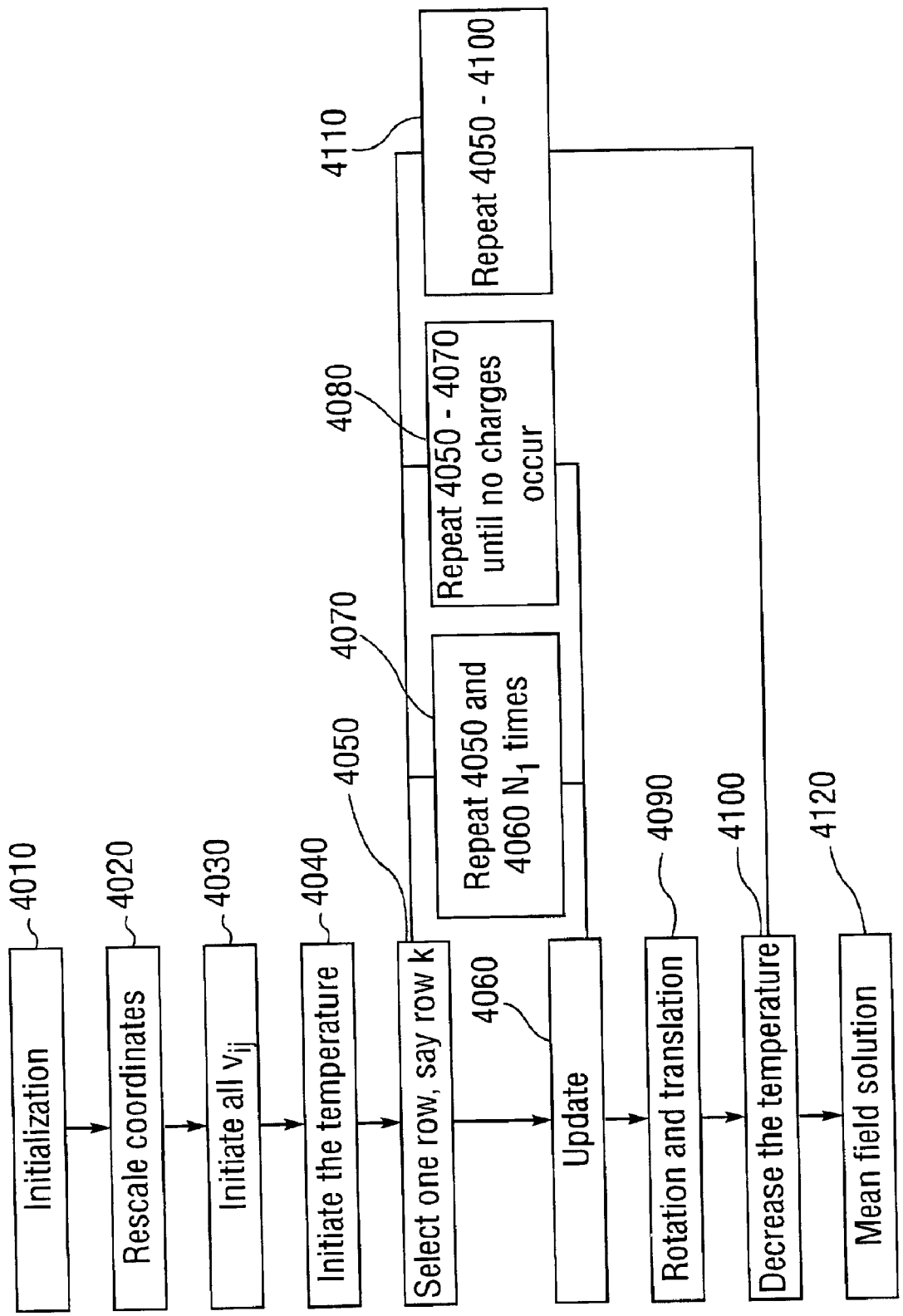
FIG. 4 illustrates algorithmic steps.

The following describes a preferred way of defining the algorithm steps as shown in FIGS. 4. However, the algorithm steps could be altered in various ways as long as step 6 through 8 in algorithm 1 and 2 are followed in the order shown in FIGS. 4 by 4060, 4070 and 4080. The shortest chain is always chosen as the one that is moved ($x_i$). The mean field variables $v_{ij}$ are updated according to EQ. 11 where, in order to improve convergence, the derivatives in EQ. 12 are replaced by finite differences (see e.g. Ohlson M. & Pi H. (1997) A study of the mean field approach to knapstack problems *Neur. Netw.* 10:263–271). This update equation accounts for all mean field variables except for the first row of V, which is updated according to $$v_{0j} = 1 - \sum_{i=1}^{N_1} v_{ij} \quad j = 1, \ldots, N_2 \qquad (21)$$

As shown in FIG. 4, the updating steps for algorithm 1 could be defined as:

Updating Steps for Algorithm 1

1. Initialization, indicated by 4010 in FIG. 4;
2. Rescale coordinates such that the largest distance between atoms within the chains is unity, indicated by 4020 in FIG. 4;
3. Initiate all vij close to 1/max($N_1$, $N_2$) (randomly), indicated by 4030 in FIG. 4;
4. Initiate the temperature (e.g. T=2), indicated by 4040 in FIG. 4;
5. Randomly (without replacement) select one row, say row k, indicated by 4050 in FIG. 4;
6. Update all $v_{kj}$, j=0, . . . , $N_2$ according to EQ. 11, indicated by 4060 in FIG. 4;
7. Repeat items 5–6 $N_1$ times (such that all rows have been updated once), indicated by 4070 in FIG. 4;
8. Repeat items 5–7 until no changes occur (defined e.g. by $1/(N_1N_2)\Sigma_{ij}|v_{ij}-v_{ij}^{(old)}|\leq 0.0001$), indicated by 4080 in FIG. 4;
9. Rotation and translation of the shortest chain using the probabilistic assignment matrix V, indicated by 4090 in FIG. 4;
10. Decrease the temperature T→εT, indicated by 4100 in FIG. 4;
11. Repeat items 5–10 until all $v_{ij}$ are close to 1 or 0 (defined e.g. by $1/N_1\Sigma_{ij}v_{ij}^2 \geq 0.99$), indicated by 4110 in FIG. 4; and
12. Finally, the mean field solution is given by the integer limit of $v_{ij}$, i.e. for each row i, i=1, . . . , N, select the column j* such that $v_{ij}$ * is the largest element for this row. Let $s_{ij}$ *=1 and all other $s_{ij}$=0 for this row. As indicated by 4120 in FIG. 4.

As also shown in FIG. 4, the updating steps for algorithm 2 could be defined as:

Updating Steps for Algorithm 2

1. Initialization, indicated by 4010 in FIG. 4;
2. Rescale coordinates such that the largest distance between atoms within the chains is unity, indicated by 4020 in FIG. 4;
3. Initiate all $v_{ij}$ close to 1/max($N_1$, $N_2$) (randomly), indicated by 4030 in FIG. 4;
4. Initiate the temperature (e.g. T=2), indicated by 4040 in FIG. 4;
5. Randomly (without replacement) select one row, say row k, indicated by 4050 in FIG. 4;
6. Update all mean field variables V(ij,k) and D(ij), indicated by 4060 in FIG. 4;
7. Repeat items 5–6 $N_1$ times (such that all rows have been updated once), indicated by 4070 in FIG. 4;
8. Repeat items 5–7 until no changes occur (defined e.g. by $1/(N_1N_2)\Sigma_{ij}|v_{ij}-v_{ij}^{(old)}|\leq 0.0001$), indicated by 4080 in FIG. 4;
9. Compute matching matrix S(ij), move protein 1 and compute new distances $d(i,j)^2$, indicated by 4090 in FIG. 4;
10. Decrease the temperature T→εT, indicated by 4100 in FIG. 4;
11. Repeat items 5–10 until all $v_{ij}$ are close to 1 or 0 (defined e.g. by $1/N_1\Sigma_{ij}v_{ij}^2 \geq 0.99$), indicated by 4110 in FIG. 4; and
12. Finally, the mean field solution is given by the integer limit of $v_{ij}$ i.e. for each row i, i=1, . . . , $N_1$ select the column j* such that $v_{ij}$ * is the largest element for this row. Let $s_{ij}$ *=1 and all other $s_{ij}$=0 for this row. As indicated by 4120 in FIG. 4.

It is important to note that while the present invention has been described in the context of a fully functional data processing system and method, those skilled in the art will appreciate that the mechanism of the present invention is capable of being distributed in the form of a computer readable medium of instructions in a variety of forms, and that the present invention applies equally regardless of the particular type of signal bearing medium used to actually carry out the distribution. In other words, the present invention is also a program storage device accessible by a computer, tangible embodying a program of instructions or means executable by the computer to perform method steps for protein structure alignments. Examples of computer readable medium include: recordable type media such as floppy disks and CD-ROMS and transmission type media such as digital and analog communication links. In addition, the present invention could be implemented and coded in different programming languages such as, but not limited to, for example C and C++ programming languages, JAVA or Java script, or DHTML The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents

What is claimed is:

1. A program storage device accessible by a computer embodying a program of instructions executable by said computer to perform method steps for protein structure alignment, comprising:

(a) receiving atomic coordinates of a first protein with $N_1$ atoms;

(b) receiving atomic coordinates of a second protein with $N_2$ atoms;

(c) making an initial alignment of said atoms of said first protein to said atoms of said second protein;

(d) calculating all atomic distances between said atomic coordinates of said atoms of said first protein and said atomic coordinates of said atoms of said second protein;

(e) defining a matrix with a plurality of binary assignment variables wherein each binary assignment variable corresponding to either a match or to a gap;

(f) defining one or more mean field equations wherein said plurality of binary assignment variables are replaced by a plurality of continuous mean field variables, whereby said each mean field variable has a value between 0 and 1, and a plurality of forces that are proportional to said atomic distances squared;

(g) formulating an energy function, wherein:
said energy function includes a first cost for each said atomic distance wherein said distance is a weighted body transformation using said continuous mean field variables of said first protein while keeping said second protein fixed,
said energy function includes a second cost $\lambda$ for each said gap by either said first protein or said second protein,
said energy function includes a third cost $\delta$ for a position-independent consecutive said gap,
said energy function includes a fourth cost for enforcing a constraint to satisfy that each said atom of said first protein either aligns with said atom of said second protein or to said gap;

(h) minimizing by an iterative process of said energy function and updating said continuous mean field variables in said mean field equations for a decreasing set of temperatures T until convergence to a predefined convergence value is reached; and (i) after convergence rounding off said continuous mean field variables to either 0 or 1.

2. The program storage device as set forth in claim 1, wherein said formulating an energy function further comprises a fifth cost for discouraging crossed matches.

3. The program storage device as set forth in claim 1, wherein said second cost is a value between 0.01 and 0.5.

4. The program storage device as set forth in claim 3, wherein said second cost $\lambda$ for a $\alpha$-site in a $\alpha$-helix has a larger said second cost $\lambda$ by a factor between 0.01 and 0.5 of said second cost $\lambda$.

5. The program storage device as set forth in claim 3, wherein said second cost $\lambda$ for a $\beta$-sheet has a larger said second cost $\lambda$ by a factor between 0.01 and 0.5 of said second cost $\lambda$.

6. The program storage device as set forth in claim 1, wherein said third cost $\delta$ is a function of said second cost $\lambda$ divided by a value between 1 and 20.

7. The program storage device as set forth in claim 1, wherein fourth cost includes a parameter $\gamma$ with a value between 0 and 0.2.

8. The program storage device as set forth in claim 1, wherein said minimizing by an iterative process includes an iteration parameter $\epsilon$ with a value between 0.5 and 0.95.

9. The program storage device as set forth in claim 1, wherein said minimizing by an iterative process further comprises the step of initiating said temperature to a value between 1 and 100.

10. A method of using a mean field approach for protein structure alignment, comprising the steps of:

(a) receiving atomic coordinates of a first protein with $N_1$ atoms;

(b) receiving atomic coordinates of a second protein with $N_2$ atoms;

(c) making an initial alignment of said atoms of said first protein to said atoms of said second protein;

(d) calculating all atomic distances between said atomic coordinates of said atoms of said first protein and said atomic coordinates of said atoms of said second protein;

(e) defining a matrix with a plurality of binary assignment variables wherein each binary assignment variable corresponding to either a match or to a gap;

(f) defining one or more mean field equations wherein said plurality of binary assignment variables are replaced by a plurality of continuous mean field variables, whereby said each mean field variable has a value between 0 and 1, and a plurality of forces that are proportional to said atomic distances squared;

(g) formulating an energy function, wherein:
said energy function includes a first cost for each said atomic distance wherein said distance is a weighted body transformation using said continuous mean field variables of said first protein while keeping said second protein fixed,
said energy function includes a second cost $\lambda$ for each said gap by either said first protein or said second protein,
said energy function includes a third cost $\delta$ for a position-independent consecutive said gap,
said energy function includes a fourth cost for enforcing a constraint to satisfy that each said atom of said first protein either aligns with said atom of said second protein or to said gap;

(h) minimizing by an iterative process of said energy function and updating said continuous mean field variables in said mean field equations for a decreasing set of temperatures T until convergence to a predefined convergence value is reached; and (i) after convergence rounding off said continuous mean field variables to either 0 or 1.

11. The method as set forth in claim 10, wherein said step of formulating an energy function further comprises a fifth cost for discouraging crossed matches.

12. The method as set forth in claim 10, wherein said second cost $\lambda$ is a value between 0.01 and 0.5.

13. The method as set forth in claim 12, wherein said second cost $\lambda$ for a $\alpha$-site in a $\alpha$-helix has a larger said second cost $\lambda$ by a factor between 0.01 and 0.5 of said second cost $\lambda$.

14. The method as set forth in claim 12, wherein said second cost $\lambda$ for a $\beta$-sheet has a larger said second cost $\lambda$ by a factor between 0.01 and 0.5 of said second cost $\lambda$.

15. The method as set forth in claim 10, wherein said third cost $\delta$ is a function of said second cost $\lambda$ divided by a value between 1 and 20.

16. The method as set forth in claim 10, wherein fourth cost includes a parameter $\gamma$ with a value between 0 and 0.2.

17. The method as set forth in claim 10, wherein said step of minimizing by an iterative process includes an iteration parameter $\epsilon$ with a value between 0.5 and 0.95.

18. The method as set forth in claim 10, wherein said step of minimizing by an iterative process further comprises the step of initiating said temperature to a value between 1 and 100.

* * * * *